(12) United States Patent
Lauer

(10) Patent No.: US 6,234,538 B1
(45) Date of Patent: *May 22, 2001

(54) CONNECTOR ELEMENT

(75) Inventor: Martin Lauer, St. Wendel (DE)

(73) Assignee: Fresenius Medical Care Deutschland GmbH, Bad Homburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/342,006

(22) Filed: Jun. 28, 1999

(30) Foreign Application Priority Data

Jun. 26, 1998 (DE) .............................. 198 28 650

(51) Int. Cl.$^7$ .............................. A61M 5/32; F16L 55/00
(52) U.S. Cl. .............................. 285/3; 285/331; 604/905
(58) Field of Search .............................. 285/3, 4, 331; 604/905

(56) References Cited

U.S. PATENT DOCUMENTS

| | | | |
|---|---|---|---|
| 3,466,065 | * | 9/1969 | Acker et al. .............................. 285/3 |
| 4,004,586 | * | 1/1977 | Christensen et al. .............................. 604/905 |
| 4,019,512 | * | 4/1977 | Tenczar .............................. 604/905 |
| 4,022,205 | * | 5/1977 | Tenczar .............................. 285/3 |
| 4,022,496 | * | 5/1977 | Crissy et al. .............................. 285/3 |
| 4,030,494 | * | 6/1977 | Tenczar .............................. 285/3 |
| 4,161,949 | * | 7/1979 | Thanawalla et al. .............................. 604/905 |
| 4,169,475 | * | 10/1979 | Genese .............................. 604/905 |
| 4,187,846 | * | 2/1980 | Lolachi et al. .............................. 604/905 |
| 4,195,632 | | 4/1980 | Parker et al. . |
| 4,256,106 | * | 3/1981 | Shoor .............................. 604/905 |
| 4,457,749 | * | 7/1984 | Bellotti et al. .............................. 604/905 |
| 4,636,204 | | 1/1987 | Christopherson et al. . |
| 5,065,783 | * | 11/1991 | Ogle, II .............................. 604/905 |
| 5,117,875 | * | 6/1992 | Marrucchi .............................. 285/3 |
| 5,122,123 | * | 6/1992 | Vaillancourt .............................. 604/905 |
| 5,492,147 | * | 2/1996 | Challender et al. .............................. 604/905 |
| 6,063,068 | * | 5/2000 | Fowles et al. .............................. 604/905 |

FOREIGN PATENT DOCUMENTS

| | | | |
|---|---|---|---|
| 1070054 | * | 11/1959 | (DE) .............................. 285/3 |
| 1300635 | * | 8/1969 | (DE) .............................. 285/3 |
| 32 10 148 | | 9/1983 | (DE) . |
| 0 775 501 | | 5/1997 | (EP) . |
| 0 830 874 | | 3/1998 | (EP) . |
| 1132443 | * | 10/1968 | (GB) .............................. 285/3 |
| WO 82/02528 | | 8/1982 | (WO) . |
| WO 94/08173 | | 4/1994 | (WO) . |
| 94008173 | * | 4/1994 | (WO) .............................. 285/3 |

* cited by examiner

Primary Examiner—Eric K. Nicholson
(74) Attorney, Agent, or Firm—Kenyon & Kenyon

(57) ABSTRACT

The present invention concerns a connector element used to connect lengths of tubing, cannulas and catheters, to a second connector element. The connector element has a conduit for conveying a flowing medium, a shut-off element by which the conduit can be sealed off, and an portion for accommodating a puncture element movable relative to the shut-off element, which is designed to open the shut-off element when the connection is established. The connector element is simple to manufacture and ensures a reliable connection, because the shut-off element is of the same material and is integral with the connector element.

17 Claims, 4 Drawing Sheets

CONNECTOR ELEMENT

BACKGROUND OF THE INVENTION

The present invention relates to a connector element for connecting tubes, cannulas and catheters, and in particular relates to a connector element for connecting tubes, cannulas and catheters that must remain sealed until the connection is completed.

DESCRIPTION OF RELATED ART

An important area of application for connectors is connecting containers of various fluids to medical machines such as a dialyzer with tubing or other types of lines, or connecting the ends of two portions of tubing for the purpose of providing extension lines. To always ensure a sterile and tight connection and thus always minimize any risk of infection to the patient, high demands are made on the design and quality of the connectors and the type of connection formed by the connectors. This is crucial to prevent any contamination not only before but also during and after the connection is made.

International Patent WO 82/02528 discloses a connection system composed of two connector elements, where the connector elements are sealed by thermoplastic membranes before the connection. On the end opposite the thermoplastic membrane, each connector element is itself connected to a length of tubing which is in turn connected, for example, to a container for holding dialysis fluids or to a dialysis machine. The connector elements have an end with a tapered point for opening the sealing membranes arranged in the tubing. While establishing the connection, first the thermoplastic membranes are joined, and then fused by using a suitable heat source, thereby forming a tight connection of the connector elements. Following that, the sealing membranes are opened by using the pointed ends of the connector elements, with the movement of the pointed ends relative to the sealing membranes being performed by a balloon-like area of the tubing. This connector includes a complex system of different membranes and connector elements, and is therefore complicated and expensive to manufacture.

International Patent WO 94/08173 describes a connector system with two connector elements sealed by membranes. After the membranes are joined, a displaceable mandrel arranged movably in one of the connector elements is guided through the membranes. In the unconnected state, the mandrel is accommodated in a space bordered by one of the membranes. Accordingly, during manufacture of the connector, it is necessary to secure the membrane to the connector element after inserting the mandrel, which makes the connector manufacturing process relatively expensive.

Unexamined German Patent 32 10 148 discloses a generic connector element having a puncture element that can be moved relative to a shut-off element in the form of an elastomeric membrane, opening the latter when the connection is made. The puncture element has a male Luer cone on its opening side, that cooperates with a corresponding female cone in making the connection. The elastomer membrane extends over the area for conveying a flowing medium and seals it when the connector element is disconnected. The membrane is in contact with one portion of the connector element, where it is kept in place by an adapter. One disadvantage of this type of connector element is that it is made of several different materials, and that the membrane must be inserted subsequently to assembly and secured with a fluid-tight seal.

SUMMARY OF THE INVENTION

The present invention is directed to a connector element for connecting tubes, cannulas, catheters and other types of fluid lines that substantially obviates one or more of the problems due to limitations and disadvantages of the related art and that can be manufactured easily and will guarantee a reliable connection.

Additional features and advantages of the invention will be set forth in the description which follows, and in part will be apparent from the description, or may be learned by practice of the invention. The objectives and other advantages of the invention will be realized and attained by the apparatus and method particularly pointed out in the written description and claims hereof, as well as the appended drawings.

To achieve these and other advantages and in accordance with the purpose of the invention, as embodied and broadly described, the invention is connector element that has a shut-off element designed as a single-material, integral component of the connector element. This design permits relatively simple manufacture of the connector elements because the shut-off element is an integral component of the connector element, and no subsequent positioning and securing of the shut-off element within the connector element is needed. Since it is not necessary to position and secure sealing membranes subsequently to assembly of the connector elements, the manufacture of the connectors is simplified and an especially tight arrangement is obtained because the connector elements and the shut-off elements can be manufactured in a single operation. Accordingly, this invention eliminates the costly procedures of subsequently attaching and testing the film membranes or membrane-fitted separate parts.

According to a preferred embodiment of the present invention, the shut-off element is designed as an injection molded membrane. The injection molded membrane can be manufactured in the same operation as the connector element, thus making it unnecessary to later attach a shut-off element of any kind to the assembly. In particular, this design according to the present invention yields an especially tight connector element, without any dead or wasted space within the connector. This not only protects against leakage and bacterial contamination, but also guarantees a permanently leak proof system that withstands up to a pressure difference of several bar.

In another embodiment of the present invention, the area or conduit for conveying the medium includes the portion for accommodating the puncture element. It is also especially advantageous if the area for conveying the medium includes a socket connector that can be secured to a corresponding socket connector of a second connector member.

In yet another embodiment of the present invention, the connector element includes a housing, and the socket connector is disposed within that housing. According to the present invention, the socket connector may be sealed by the shut-off element, for example a membrane, thereby ensuring that the connected tubing or containers attached to the connector will be leakproof and sterile. The shut-off element in this arrangement is punctured or opened by the puncture element when the connection is established. The housing can serve to protect the socket connector and the shut-off element from unwanted touching or contact, which can result in the introduction of contaminants. The housing diameter may be preferentially designed in such a way that it is impossible to inadvertently touch the socket connector or the areas of the connector element that will be exposed to liquid or gas media after the connection is established.

It is especially advantageous if the attachment member includes a puncture element that can be inserted into the socket connector and secured to it by using a lock. The lock may include a groove extending circumferentially from the outer surface of the puncture element, and a projection extending circumferentially from the inside surface of the socket connector. The puncture element may be inserted into the socket connector and held in the desired position by the lock before the connection is made, and during certain phases of the connection.

According to a preferred embodiment of the present invention, the puncture element is designed in such a way that it can be released from the lock by a force applied by a socket connector of a second connector element, as it is connected to the first connector element. In this manner, the puncture element is released from its lock only when the connection is established, and is moved by the second element socket connector in such a way that the shut-off element is punctured or opened. The lock can be advantageously designed so that first the shut-off element of one of the connector elements is punctured, before the corresponding socket connector releases the puncture element from its lock, and then the second shut-off element of the second connector element is punctured. The puncture element can be released from its lock by providing a projection extending from the puncture element that cooperates with the socket connector of the second connector element as it is joined to the first connector element.

In a further embodiment of the present invention, the housing and the socket connector of a second connector element can be accommodated at least in part within the housing and the socket connector of the first connector element, as the two connector elements are brought together to form the connection. This can be achieved, for example, by appropriate sizing of the inside and outside diameters of the parts of both connector elements.

It is especially advantageous if the socket connector is tapered at the end portion facing the second connector element. This facilitates the insertion of one of the socket connectors into the corresponding female socket connector of the other connector element, resulting in an advantageous elastic widening of the female socket connector as the connection is made, which ensures an especially tight connection of the two socket connectors. The connecting and, if necessary, the disconnecting operations can be performed by hand or by machine. It is further advantageous if the disconnection operation requires a greater force applied to the connector elements than the connection operation. If necessary, structural elements can be integrated, for example by injection molding during the manufacture, to make it impossible to disconnect the parts once they have been connected. It is also advantageous for the puncture element to have an essentially cylindrical shape and be tapered to form a point at its ends. This makes it relatively simple to open the shut-off elements or membranes without requiring much force. It is also possible to design the puncture element with ends shaped like a notch, a perforation, or in a star-shaped profile.

In yet another embodiment of the present invention, the connector element and the puncture element are designed as injection molded parts that can be manufactured inexpensively in manifold injection dies. This permits simple manufacture of the parts in a variety of possible designs. In one example according to the invention, the connector element with the shut-off element and the puncture element are made of polypropylene.

According to a further preferred embodiment of the present invention, the housing of the connector element and the tube connection portion that attaches the connector element to a tube have cylindrical inner and outer surfaces, that define a substantially cylindrical shell. This has the advantage that no rotational positioning is required in either the manufacture or use of the connector system. Instead, the connection can be established by simply inserting one of the connector elements into the other connector element. With appropriate design and sizing of the housing of the connector elements, it is possible to achieve especially good contact protection. As an example, dimensions of for the inside diameter of the housing that have given good results are approximately 8.6 mm for the female connector element and 7.4 mm for the male connector element. These dimensions also guarantee good protection against contact and damage to the connection element due to fingertips and fingernails.

According to the present invention, it is especially advantageous if the inner or outer surfaces of the socket connectors are tapered or conical in design. This offers the advantage that a tight connection between two connecting elements is achieved, even before the shut-off elements have punctured the connector elements.

The end areas of the socket connectors preferably may include a peripheral projection extending from their inner or from their outer surface, by which a tight connection can be established with a corresponding male or female socket connector of a second connector element. In this manner, the connection is sealed from the ambient atmosphere before the shut-off elements or membranes are punctured. Accordingly, the sterility before, during or after the connection is not compromised by pressure or a vacuum differentials between the portions of the connector elements or between the connector and the environment. Despite the pressure differences between the connector elements, which may be on the order of up to several bar depending on the dimensions of the arrangement, a tight connection is always established between the connector elements to be joined before the sealing membranes are punctured.

In yet a further embodiment of the present invention, the shut-off element and the portion of connector element accommodating the puncture element are arranged in such a way that the puncture element can be inserted from the connection side of the connector element. The term "connection side" is to be understood as referring to the side of the connector element where a second connector element is to be inserted or attached, so that the two connector elements are joined together. This arrangement is especially advantageous when one of the connector elements is an integral part of an injection molded device. For example, the connector element could be manufactured together with such device, which could then be connected to tubing by using a second connector element attached to the tubing. Such device could be, for example, a device to control the flow and to treat various fluids. If several connector outlets leading in various directions from a wall of a cassette-like device are required, the shut-off element or membrane could be arranged, for example, so that the puncture element can be inserted from the outside or from the connection side of the connector element.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are incorporated in and constitute a part of this specification, illustrate an embodiment of the invention and, together with the description, serve to explain the objects, advantages, and principles of the invention. In the drawings.

DETAILED DESCRIPTION OF THE INVENTION

Figure 1:
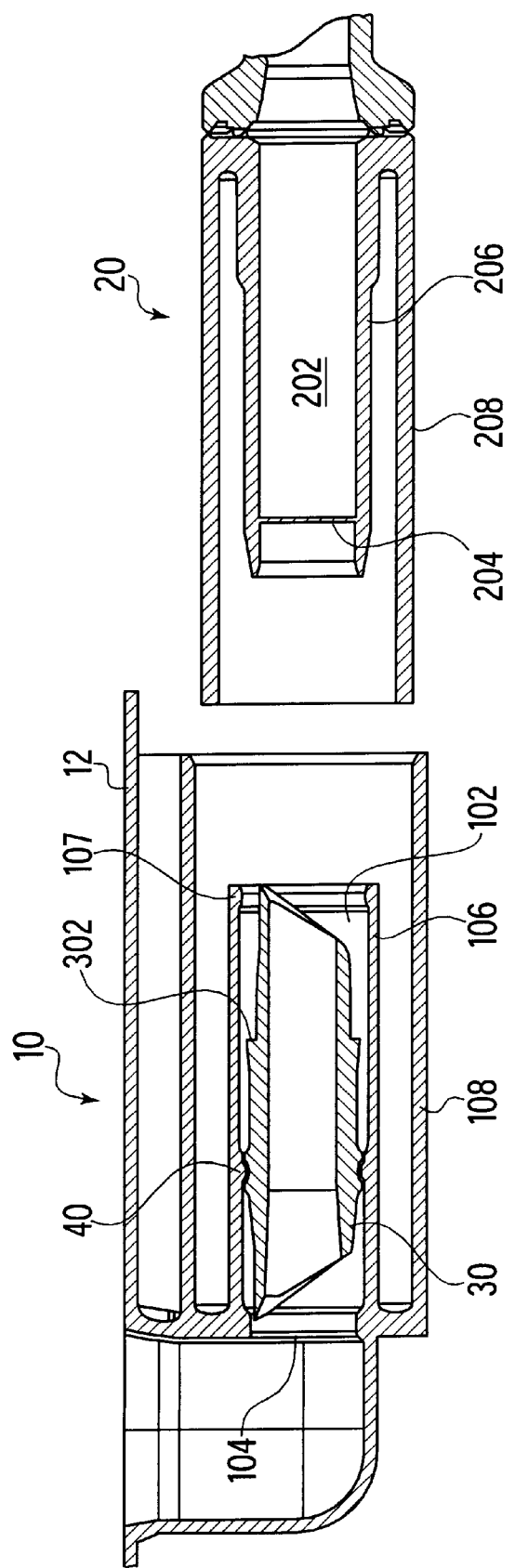
FIG. 1 is a cross sectional view showing two connector elements according to the present invention in an initial position before the connection is started.

FIG. 1 shows two connector elements 10, 20 in an initial position before being joined. Connector element 10 has a housing 108 which encloses a socket connector 106 extending essentially in the same direction as the housing. An opening is provided on one end of the housing 108 to receive, for example, a length of tubing, as shown on the left of connector element 10 in FIG. 1. This opening and the portion of connector element 10 on the inside of socket connector 106 define a conduit (conduit portion) 102 for conveying a flowing medium, such as a liquid or a gas. Conduit 102 is tightly sealed by a membrane 104 which serves as a shut-off element.

Puncture element 30 of connector element 10 is accommodated in socket connector 106 and is held in a desired position in socket connector 106 by lock 40. In a preferred embodiment according to the invention, lock 40 consists of a projection which extends circumferentially from the inside surface of socket connector 106 and engages a corresponding peripheral groove formed circumferentially on the outside surface of puncture element 30. Puncture element 30 has a peripheral projection 302 formed on its outer surface.

Connector element 20 has a housing 208 accommodating socket connector 206. A length of tubing or any desired ducting attached to working means may be connected to the portion of housing 208 shown on the right in FIG. 1. Socket connector 206 and the opening of housing 208 into which a length of tubing may be attached form the conduit 202 for conveying a flowing medium. This conduit is tightly sealed on one side by a membrane 204 which serves as a shut-off element for socket connector 206. Membrane 204 thus provides a tight and reliable cut-off for connector element 20 and prevents unwanted penetration of contaminants in the conduit.

A peripheral projection 107 is provided in the end area of socket connector 106, where connector element 10 first contacts connector element 20. Projection 107 serves to establish a tight connection between socket connectors 106 and 206, that are respectively part of connector elements 10 and 20, while the two connector elements 10, 20 are being connected. In this manner a seal against the outside environment is achieved before the shut-off elements 104, 204 are punctured, thereby ensuring the sterility and imperviousness of the connection before, during and after establishing the connection.

Membranes 104, 204 are designed as single-material injection molded membranes that are hermetically sealed and free of dead space, and are integral with the connector elements. The membranes 104, 204 are manufactured simultaneously with the connector elements 10, 20. The connectors according to the invention are thus relatively simple to manufacture, and the membranes are highly reliable. In particular, subsequent welding operations to provide film membranes or other shut-off elements and the associated testing become superfluous. Instead, during the start-up phase of mass production, 100% of the injection molded membranes according to the present invention can be tested for integrity by simple pressure tests, and later they can be tested randomly. These test as well as additional tests of properties of the connector element can be advantageously performed by the supplier of the injection molded parts, or in specialized quality control laboratories. As a result, it is unnecessary to test the components at the main assembly line, or to test membranes that were added subsequently to manufacturing the rest of the connector element. Moreover, the connector element according to the invention eliminates the need to separate rejected connectors on the main assembly line. In a preferred embodiment, the injection molded membranes forming shut-off elements 104, 204 typically can have a thickness of approximately 0.2 mm.

According to one embodiment of the invention, connector element 10 is an integral part of a cassette-like structural component used as a fluid carrier or as a fluid treatment device, and is manufactured together with the component. As shown in FIG. 1, wall 12 of the cassette-like component is disposed directly above housing 108. Conduit 102 for accommodating puncture element 30 and the shut-off element 104 are arranged so that the puncture element can be inserted in the conduit 102 from the connection side of connector element 10, to permit the outlet of connector element 10 to extend in any desired direction relative to cassette wall 12. This arrangement allows to orient the connection in any desired direction relative to the cassette-like component, while allowing easy insertion of the puncture element 30 in the connector element.

To ensure a wide range of applications for such a cassette-like component, it is especially advantageous to insert puncture element 30 into connector element 10 that is attached to the cassette. This is necessary in particular if the second connector element to be joined to the connector element on the cassette side is not attached to a disposable item, such as a length of tubing, but rather forms a connection to a machine, and is therefore not changed routinely.

Figure 2:
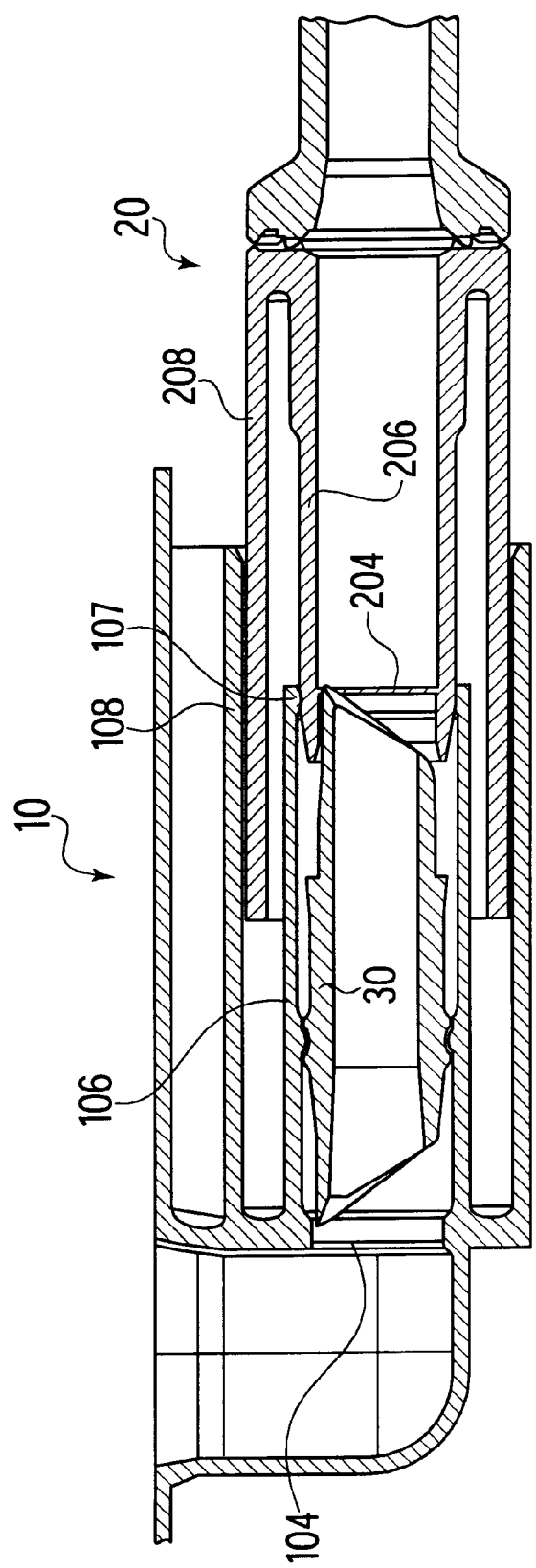
FIG. 2 is a cross sectional view showing two connector elements in a first intermediate position as the membrane is in contact with the puncture element.

Connector elements 10 and 20 are joined starting from the positions illustrated in FIG. 1. Housing 208 is inserted first within housing 108, and then socket connector 206 of connector element 20 enters socket connector 106 of connector element 10, until shut-off element 204 contacts the right side portion of puncture element 30, as shown in FIG. 2. When the elements are joined, housing 208 is inserted into housing 108 and socket connector 206 is inserted into socket connector 106. To facilitate this insertion, the end areas of socket connectors 106, 206 are tapered.

In addition to the arrangement illustrated in FIG. 2, it is also possible for housing 108 and socket connector 106 to be accommodated in the corresponding portions of connector element 20. It is also possible for puncture element 30 to be arranged in second connector element 20 instead of in the first connector element 10.

While connector elements 10, 20 are being joined, the peripheral projection 107 of socket connector 106 becomes engaged with the outside surface of the inserted socket connector 206 of connector element 20. This ensures that a seal with respect to the ambient atmosphere is achieved before shut-off elements 104, 204 are punctured.

Figure 3:
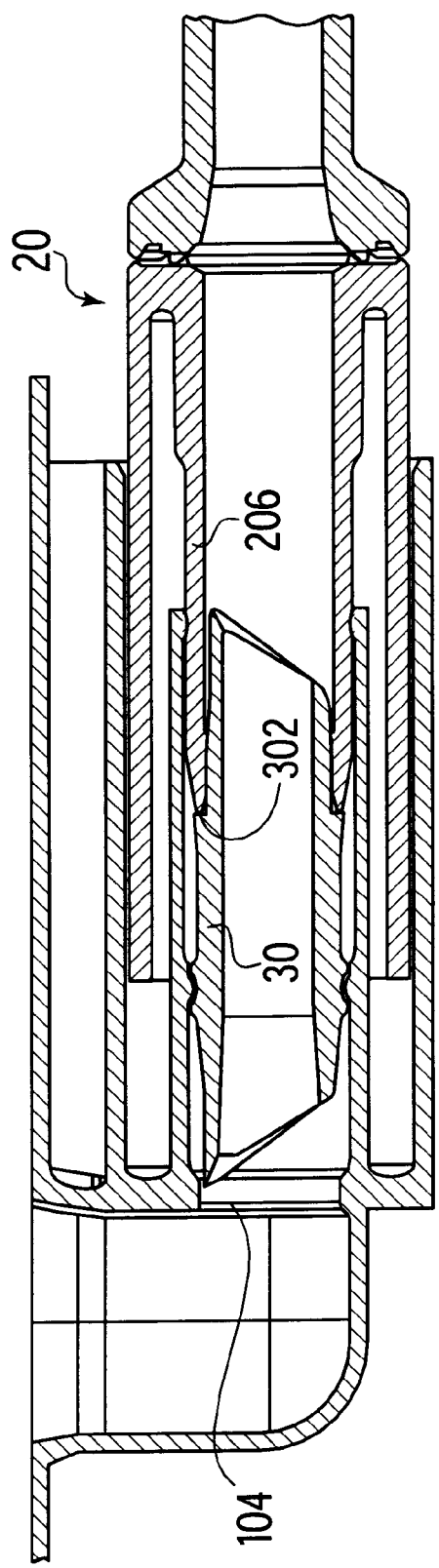
FIG. 3 is a cross sectional view showing two connector elements in a second intermediate position where the membrane of the connector element shown on the right has been opened.

As the connector elements continue to be joined starting from the positions shown in FIG. 2, the condition illustrated in FIG. 3 is reached, where the right pointed edge of puncture element 30 has punctured the shut-off element of connector element 20. Furthermore, at the same time the end area of socket connector 206 is in contact with projection 302 of puncture element 30. At this stage, one of the shut-off element membranes 204 has already been punctured, while the other shut-off element 104 is still sealed. This condition is reached because puncture element 30 is held in the locked position until it reaches the condition illustrated in FIG. 3.

Figure 4:
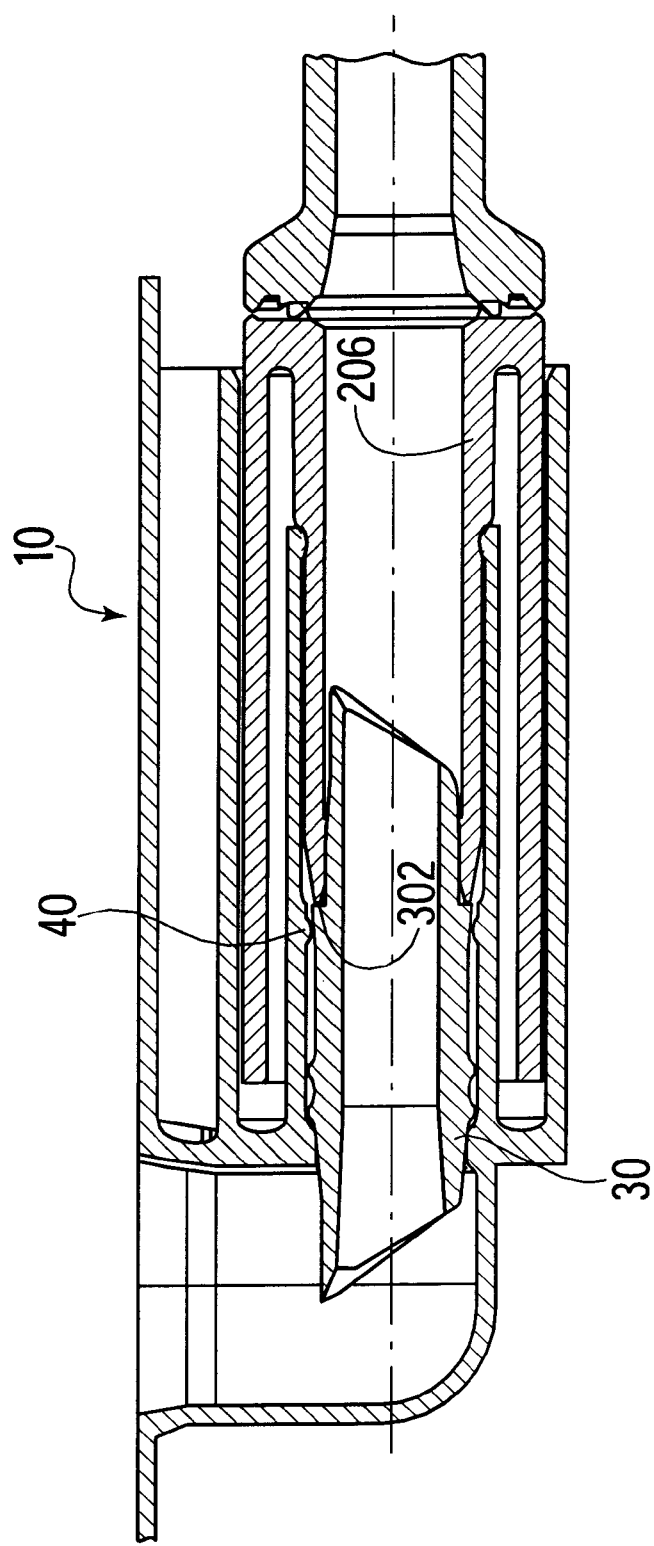
FIG. 4 is a cross sectional view showing two connector elements in a connected position where both membranes have been opened.

From this point, any further movement to join together connector elements 10 and 20 leads to the arrangement illustrated in FIG. 4. The force applied by the front end of socket connector 206 on the projection 302 of puncture element 30 releases puncture element 30 from lock 40, and causes it to puncture the shut-off element membrane 104 with its pointed end. This set of actions thus forms a reliably sealed and sterile passage between connector elements 10 and 20.

In addition to the embodiment illustrated in FIGS. 1 through 4, a further embodiment according to the invention of the connector elements may also be designed, so that shut-off element 104 of connector element 10 is punctured first, and shut-off element 204 of second connector element 20 is punctured next. This sequence requires that puncture element 30 not be in contact with a stop after shut-off element 104 is punctured, thereby permitting relative movement between puncture element 30 and shut-off element 204 of connector element 20.

In a further embodiment according to the invention, the inside diameter of housings 108, 208 may be selected advantageously so that effective protection of the conduits 102, 202 from contact is achieved, because it is impossible to touch those portions with a user's fingers. In a preferred embodiment, the female connector element has an inside diameter of approximately 8.6 mm, and the male connector element has an inside diameter of approximately 7.4 mm. Typical values for the outside diameter and the depth of insertion of the connector element to be inserted are, for example, approximately 8.4 mm and at least 22 mm, respectively.

The connector element according to the present invention guarantees imperviousness from contamination before, during and after the connection between two connector elements is formed. A reliable connecting procedure is equally obtained whether the connectors are filled with a liquid or a gas. Subsequent repeated connections and disconnections during use are also possible, and the direction of flow does not have any effect on the connector elements.

It will be apparent to those skilled in the art that various modifications and variations can be made in the structure and methodology of the present invention, without departing from the spirit or scope of the invention. Thus, it is intended that the present invention cover the modifications and variations of this invention provided they come within the scope of the appended claims and their equivalents.

What is claimed is:

1. A connector element for connecting a fluid line to a second connector element, comprising:
    a conduit portion for conveying a flowing medium;
    a shut-off element integral with and made of the same material as the connector element, the shut-off element being adapted to seal off the conduit portion;
    a socket connector disposed in the conduit portion; and
    a puncture element disposed in the conduit portion and movable relative to the shut-off element, the puncture element being adapted to open the shut-off element while establishing a connection to the second connector element, the puncture element being adapted to be inserted into the socket connector and to be releasably secured to the socket connector by a lock.

2. The connector element according to claim 1, wherein the shut-off element is an injection molded membrane.

3. The connector element according to claim 1, wherein the conduit for conveying the medium comprises a chamber for accommodating the puncture element.

4. The connector element according to claim 1, further comprising an outer housing containing the socket connector.

5. The connector element according to claim 1, wherein the lock comprises a circumferential groove formed on an outer surface of the puncture element and a projection extending from an inner surface of the socket connector.

6. The connector element according to claim 1, wherein the puncture element is adapted to be releasable from the lock by a force applied by a corresponding second socket connector of the second connector element, upon connection with the connector element.

7. The connector element according to claim 6, wherein the puncture element comprises a projection disposed on an outside circumference of the puncture element, adapted to be connected to the socket connector of the second connector element.

8. The connector element according to claim 4, wherein the housing and the socket connector of the connector element are dimensioned to fit around at least a portion of respectively a second housing and a second socket connector of the second connector element.

9. The connector element according to claim 1, wherein the socket connector has a tapered end portion.

10. The connector element according to claim 1, wherein the puncture element has a substantially cylindrical shape and has end portions tapered to a point.

11. The connector element according to claim 1, wherein the conduit portion and the puncture element are injection molded parts.

12. The connector element according to claim 1, wherein the connector element, the shut-off element, and the puncture element are formed of polypropylene.

13. The connector element according to claim 4, wherein the housing and the socket connector are substantially cylindrical shells.

14. The connector element according to claim 1, wherein one of the inner and outer surfaces of the socket connector are tapered or conical.

15. The connector element according to claim 1, wherein the socket connector comprises a peripheral projection extending from an end portion of the socket connector, adapted to form a tight connection with a portion of the second connector element.

16. The connector element according to claim 1, wherein the shut-off element and the conduit are adapted to accommodate the puncture element so that the puncture element can be inserted in the connector element from a connection end of the connector element.

17. A method for connecting a first fluid line to a second fluid line, comprising:
    attaching a first connector element to the first fluid line and a second connector element to the second fluid line;
    pushing a housing of the second connector element into a housing of the first connector element so that a recessed socket connector of the first connector element forms a continuous conduit with a recessed socket connector of the second connector element; and further pushing the housing of the second connector element into the housing of the first connector element so that a puncture element of the first connector opens shut-off elements of the first and second connector elements.

* * * * *